United States Patent [19]

Khoobiar

[11] 4,169,070

[45] Sep. 25, 1979

[54] CATALYST AND PROCESS FOR PRODUCING UNSATURATED ACIDS BY USING SAME

[75] Inventor: Sargis Khoobiar, Kinnelon, N.J.

[73] Assignee: Halcon Research and Development Corporation, New York, N.Y.

[21] Appl. No.: 895,676

[22] Filed: Apr. 12, 1978

[51] Int. Cl.$^2$ ............................................. B01J 21/02
[52] U.S. Cl. ....................................... 252/432; 562/547
[58] Field of Search ......................................... 252/432

[56] References Cited

U.S. PATENT DOCUMENTS

| | | |
|---|---|---|
| 3,172,909 | 3/1965 | Callahan et al. ................ 252/432 X |
| 3,326,817 | 6/1967 | Callahan et al. ................ 252/437 X |
| 3,567,772 | 3/1971 | Yanagita et al. ................ 252/432 X |
| 3,838,067 | 9/1974 | Barker .................................. 252/432 |
| 3,976,688 | 8/1976 | Akiyama et al. ................ 252/432 X |
| 3,998,876 | 12/1976 | Kato et al. ........................ 252/432 X |
| 4,000,088 | 12/1976 | Shimizu et al. ................ 252/435 X |
| 4,045,478 | 8/1977 | Umemura et al. .............. 252/432 X |
| 4,051,180 | 9/1977 | Shaw et al. ...................... 252/432 X |
| 4,065,468 | 12/1977 | Grasselli et al. ................ 252/432 X |

FOREIGN PATENT DOCUMENTS

| | | | |
|---|---|---|---|
| 1900111 | 8/1970 | Fed. Rep. of Germany | ........... 252/432 |
| 2353131 | 4/1975 | Fed. Rep. of Germany . | |
| 1430337 | 3/1976 | United Kingdom . | |

*Primary Examiner*—Delbert E. Gantz
*Assistant Examiner*—William G. Wright
*Attorney, Agent, or Firm*—William C. Long; David Dick; Harold N. Wells

[57] ABSTRACT

A catalyst composition useful for the oxidation of unsaturated aldehydes, particularly the oxidation of acrolein and methacrolein to produce the corresponding unsaturated acids, acrylic acid and methacrylic acid, respectively, comprises the combination of oxides of molybdenum, copper, boron, phosphorus and antimony, an alkali metal, and optionally vanadium in predetermined relative atomic ratios. When the catalyst is used for the vapor-phase oxidation of the aldehydes with molecular oxygen, the acids are produced with a combination of good conversion and high selectivity with elevated quantities of aldehyde in the feed and at super atmospheric pressures.

3 Claims, No Drawings

CATALYST AND PROCESS FOR PRODUCING UNSATURATED ACIDS BY USING SAME

This invention relates to catalysts, and is more particularly concerned with catalysts for the vapor-phase oxidation with molecular oxygen of unsaturated aldehydes to the corresponding unsaturated acids of the same number of carbon atoms, and to a process for using such catalysts. The catalysts and process of this invention are particularly useful in the oxidation of acrolein and methacrolein to acrylic acid and methacrylic acid, respectively.

It is well known that unsaturated acids, such as acrylic acid and methacrylic acid, can be produced by the vapor-phase oxidation of the corresponding unsaturated aldehydes by means of molecular oxygen in the presence of a suitable oxidation catalyst. A variety of catalyst compositions have been proposed for this purpose and many such compositions comprise the oxides of molybdenum and phosphorus in association with the oxides of various other elements, both metallic and non-metallic. As a general rule, however, it has been difficult to achieve the combination of good conversion, i.e., reaction of a large molar proportion of the aldehyde fed, with a high selectivity, i.e., the production of a large molar quantity of unsaturated acid per mole of aldehyde converted, when catalyst compositions of this type have been used on feeds with elevated aldehyde concentration at superatmospheric pressures.

For Example, British Pat. No. 1,430,337 and U.S. Pat. No. 4,000,088 propose the use of a catalyst composition in which the oxides of molybdenum and phosphorus are combined with the oxides of antimony, copper and chromium. German Offenlegungsshrift No. 2,353,131 and U.S. Pat. No. 3,998,876 combine the oxides of molybdenum and phosphorus with the oxides of an alkali metal and arsenic plus and/or vanadium, copper with tungsten, iron, manganese and tin being disclosed as substitutes or supplements for copper or vanadium. Belgian Pat. No. 823,897 also discloses catalysts based on a combination of the oxides of molybdenum, phosphorus, an alkali metal and arsenic, vanadium and copper, with cobalt, antimony, bismuth and zirconium being disclosed as substitutes or supplements for copper or arsenic. Included among the examples are mixtures of the oxides of molybdenum, phosphorus, an alkali metal and vanadium together with copper and cobalt or copper and antimony. In other words, the catalysts of Belgian Pat. No. 823,897 correspond to the catalysts of U.S. Pat. No. 3,998,876 except that cobalt, antimony, bismuth and zirconium are equated with the arsenic of the U.S. patent but the results of the best experiments described in Belgian No. 823,897 are poorer than some of the results illustrated in U.S. Pat. No. 3,998,876. The compositions of all of these patents, however, as reported in the specific examples, gave results which indicate substantial production of carbon oxides, even with feeds of relatively low aldehyde content, i.e., 5 volume percent or less Callahan et al. U.S. Pat. Nos. 3,172,909 and 3,326,817 disclose a catalyst composition in which boron is combined with molybdenium and phosphorus. The disclosed data using the catalyst, however, refer to operations yielding very low conversions.

It is, accordingly, an object of this invention to provide a novel and improved catalyst composition which is effective in converting unsaturated aldehydes to the corresponding unsaturated acids while realizing high selectivity at elevated conversion with feeds of high aldehyde content.

It is further object of the invention to provide a process for converting unsaturated aldehydes such as acrolein and methacrolein to acrylic acid and methacrylic acid, respectively, with minimum formation of undesired byproducts such as carbon monoxide and carbon dioxide.

Other objects of the invention will be apparent from the following detailed description of the catalyst composition and process which characterize the invention.

It has been discovered that the desired high-selectivity conversion to the corresponding unsaturated acid of an unsaturated aldehyde in feeds containing more than 5 volume percent of the aldehyde can be effected by using for the vapor-phase molecular oxidation of the aldehyde a catalyst composition which comprises oxides of molybdenum, copper, boron, phosphorus, antimony, an alkali metal, and optionally vanadium, in predetermined relative atomic ratios. More specifically, the catalyst composition of the invention comprises the oxides of the above specified elements in the following atomic ratios: Mo=12, Cu=0.05-3, B=0.001-3, P=0.1-5, Sb=0.01-1, V=0-5 and X=0.05-5, wherein X is an alkali metal, i.e., a metal of Group IA of the Periodic Table, such as sodium, potassium and cesium. Preferably, the amount of Sb is 0.2-0.4, most preferably 0.3, the amount of X is preferably at least 0.3 and the amount of B is preferably at least 0.01, most preferably at least 0.1. The catalyst composition may be regarded either as a mixture of oxides of the named elements or as oxygen-containing compounds of the elements. As prepared and/or under the reaction conditions, the catalyst may contain either or both forms. The catalyst composition of the invention may, then, be expressed by the following general formula:

$$Mo_a\ Cu_b\ B_c\ P_d\ Sb_e\ V_f X_g\ O_h$$

wherein a to g indicate the atomic ratio of each component and, when a is 12, b is 0.05-3, c is 0.001-3, d is 0.1-5, e is 0.01-1, f is 0-5, g is 0.05-5 and h has a value which is determined by the valence and proportions of the other elements in the catalyst.

The catalyst composition is preferably used in unsupported form, e.g. in the form of pellets or other like compressed shapes of various sizes. The composition may be formed in conventional manner using techniques well known to persons skilled in the art. For example, compounds of molybdenum, copper, boron phosphorus, antimony, the alkali metal and optionally vanadium are dissolved in a small amount of water or other solvent, and the solutions are then combined and evaporated to dryness, e.g. in a rotary dryer. To prepare the catalyst the several components can be introduced into solution in the form of various salts or other compounds of convenient types and no specific form for the catalyst precursors is necessary. The use of ammonium salts, halides, e.g. chlorides, nitrates or acid forms of the elements, e.g. phosphoric acid are, however, particularly suitable. Preferably, however, aqueous solutions are employed and water-soluble forms of the elements are used. In some cases the solutions may have acids and/or bases added to them to facilitate disolution of the catalyst precursors. For example, acids such as hydrochloric or nitric acid, or bases such as ammonium hydroxide, can be used if desired. The resulting powder from the evaporation is then thoroughly dried and preferably screened to eliminate large particles which make it difficult to produce uniform compressed shapes, such as pellets. Typically, the powder is passed through a 20-mesh screen. The powder is then mixed with an organic binder which can be of any conventional type, such as polyvinyl alcohol, and the mixture is thoroughly dried and again screened, typically to provide a 20–80 mesh size. The dried mixture is then preferably combined with a lubricant, again of any conventional type, such as stearic acid, and compressed into the desired shape, e.g. pelletized, the compressed shapes typically having heights and diameters of 1/16 inch to ⅜ inch. Finally, the thus produced catalyst composition is activated at high temperature for a prolonged period in accordance with conventional practice in this art. For example and typically, the pellets are placed in an oven or kiln, or in a tube through which air is passed, at an elevated temperature (e.g. 300°–500° C., preferably 325°–450° C.) for at least ten hours. In a particularly preferred activation step, the temperature is raised at the rate of 20° C. per hour to 400°–450° C. and this temperature is maintained for 16 hours.

It will be understood that the foregoing description regarding preparation of the catalyst in a form suitable for use in a vapor-phase oxidation reaction is merely illustrative of many possible preparative methods and is given solely by way of exemplification. This method is, however, particularly suitable and is preferred.

When the catalyst of this invention is used in the vapor-phase oxidation of unsaturated aldehydes to form the corresponding unsaturated acids, the oxidation conditions employed are those generally associated with this reaction. Thus, the reaction in which the catalyst compositions of this invention are of particular utility and in which they provide high conversions and selectivities involves contacting the desired aldehydes, e.g. acrolein or methacrolein, in the vapor phase with the catalyst and oxygen, preferably also in the presence of steam. Once reaction is begun, it is self-sustaining because of its exothermic nature. A variety of reactors will be found to be useful and multiple tube heat exchanger type reactors are quite satisfactory, and the process can be carried out in conventional equipment commonly employed for reactions of this type.

The gaseous feed to the reactor contains appropriate concentrations of aldehyde, oxygen and steam. Suitably, an inert gas, such as nitrogen, is also present. The oxygen is usually added as such or as air enriched with oxygen. As mentioned, conventional oxidation conditions can be employed but it is a feature of the catalyst of this invention that the aldehyde can be present in concentrations of more than 5 up to about 20 volume percent of the total feed with a preferred range of more than 5 up to about 15 volume percent. In general at least 6.4 volume percent of the aldehyde is used in the feed. The corresponding ranges for oxygen are 3 to 15 volume percent, preferably 5 to 12 volume percent and for steam up to 50 volume percent, preferably 5 to 35 volume percent, the balance being the inert gas or gases.

The temperature of the reaction at the center of the reactor should, for best results, be within the range of from about 270° to 450° C., preferably 280°–400° C. and the optimum temperature range is 290° to 325° C. Because the reaction is exothermic, means for conducting the heat away from the reactor are normally employed. The temperature may be controlled by conventional methods such as by the use of reactors surrounded by a salt bath.

The pressure in the reactor is not generally critical, and the reaction may be conducted at atmospheric, superatmospheric or subatmospheric pressure. Preferably, however, pressures, ranging from atmospheric up to 100 psig, preferably up to 75 psig, and most preferably up to 50 psig are employed.

The catalyst and the processes of the present invention are useful for the production of unsaturated acids by oxidation with molecular oxygen of unsaturated aldehydes generally. The preferred starting materials are the monoethylenically unsaturated aliphatic monoaldehydes of from 3 to 6 carbon atoms, such as acrolein, methacrolein, crotonaldehyde, 2-methyl-2-butenal, and the like. Best results have been obtained with methacrolein. Mixtures of aldehydes may be used.

The unsaturated acid product may be recovered by a number of ways well known to those skilled in the art. For example, the acid may be condensed, or scrubbed with water or other suitable solvents, followed by separation of the unsaturated acid product from the scrubbing liquid. The gases remaining after the acid-removal step are suitably recycled to the reaction, if desired, preferably after removal of net CO and $CO_2$ by conventional means, e.g., absorption in aqueous sodium hydroxide solution.

The features of the invention will be more readily apparent from the following specific examples of typical application. It will be understood, however, that these examples are for the purpose of illustration only and are not to be interpreted as limiting the invention.

EXAMPLE I

In 400 cc of water are dissolved 318 grams of $(NH_4)_6Mo_7O_{24}4H_2O$. Then 11.1 grams of $Cu(NO_3)_2.3H_2O$ are dissolved in 100 cc of water, 5.26 grams of $NH_4VO_3$ are dissolved in 400 cc of water, 3 grams of $H_3BO_3$, 29.2 grams of $CsNO_3$ are dissolved in 100 cc of water, 10.2 grams of $SbCl_3$ are dissolved in a mixture of 16 cc of water, and 5 cc of concentrated HCl and 17.2 grams of $H_3PO_4$ are dissolved in a mixture of 100 cc of water, and 60 cc of 58% ammonium hydroxide. These solutions are fed to a rotary dryer of 4000 cc capacity along with 300 cc of 58% $NH_4OH$ and the mixture in the dryer is evaporated to dryness at a temperature of 150° C. The resulting powder is removed from the dryer and dried in an oven at 150° C. for 18 hours. The dried powder is screened through a 20-mesh screen, a 4% aqueous solution of polyvinyl alcohol is added in sufficient quantity to make a damp mixture and this mixture is dried at 80°–90° C. for hours. The dried mixture is then screened to 20–80 mesh, and about 2–6% of stearic acid powder is thoroughly mixed with it. The resulting mixture is then pelletized to form pellets of 3/16 inch height and diameter in which the catalyst components molybdenum, copper, vanadium, boron, cesium, antimony and phosphorus are present in the atomic ratio of 12, 0.3, 0.3, 0.3, 1, 0.3 and 1, respectively. The pellets are then activated in an oven by heating them gradually at a rate of 20° C. per hour to 350°–400° C. and maintaining them at this temperature for 16 hours. The activated pellets have a density of 0.97 gm/cc.

A 150 cc quantity of this catalyst composition is placed in a reactor defined by a ½"×90" stainless steel pipe, the reactor pipe being filled with 50 cc of inert filler (silicon carbide) below the catalyst bed and 100 cc of the inert filled above the catalyst bed in conventional manner to insure uniform temperature contact with the catalyst. Nitrogen-diluted mixtures containing methacrolein, oxygen and steam are fed to the reactor at a pressure of 15 psig, at temperatures ranging from 301° C.-304° C. and at a space velocity of about 1200 hr.$^{-1}$. The term "space velocity" is used in its conventional sense to mean liters of gas (STP) per liter of catalyst per hour. The feed composition is approximately, by volume, 7% methacrolein, 9% oxygen and 22% steam, the balance being nitrogen, determination being made on a wet basis. The reaction is run continuously with continuous feed and continuous withdrawal of exit gas but the exit gas is analyzed at intervals of several hours to give the overall effect of a series of different runs. Analyses are carried out by means of gas chromatography and by absorption in sodium hydroxide solution, using conventional techniques. The conditions of operation and the results of these experiments are set forth in the following Table A.

TABLE A

| Exp. No. | Temp. °C. | Time, hr. | Conversion, % | Selectivity methacrylic acid | acetic acid | CO + $CO_2$ |
|---|---|---|---|---|---|---|
| 1 | 301 | 19 | 53 | 83.3 | 3.82 | 0.37 |
| 2 | 302 | 27 | 54 | 82.8 | 4.07 | 0.45 |
| 3 | 302 | 31 | 58 | 84.3 | 4.34 | 0.42 |
| 4 | 303 | 38 | 45 | 86.2 | 3.66 | 0.25 |
| 5 | 302 | 42 | 50 | 86.1 | 3.87 | 0.26 |
| 6 | 302 | 86 | 66 | 85.3 | 4.02 | 0.37 |
| 7 | 302 | 88 | 62 | 85.9 | 4.44 | 0.37 |
| 8 | 302 | 90 | 50 | 85.4 | 4.05 | 0.34 |
| 9 | 302 | 94 | 59 | 86.4 | 3.88 | 0.30 |
| 10 | 303 | 96 | 60 | 87.9 | 4.13 | 0.27 |
| 11 | 304 | 98 | 57 | 87.0 | 4.16 | 0.37 |
| 12 | 304 | 100 | 66 | 85.8 | 4.26 | 0.35 |
| 13 | 302 | 102 | 63 | 87.3 | 4.23 | 0.34 |
| 14 | 303 | 110.5 | 66 | 87.1 | 4.20 | 0.29 |
| 15 | 304 | 112.5 | 65 | 86.8 | 4.07 | 0.29 |

EXAMPLE II

A catalyst is prepared as described in Example I except that the vanadium component is omitted and in the resulting catalyst, the components molybdenum, copper, boron, antimony, cesium and phosphorus are present in the atomic ratios of 12, 0.3, 0.3, 1, 0.3 and 1, respectively. The oxidation is carried out as described in Example I except that the temperature ranged from 302° C. to 306° C. The results of these experiments are set forth in Table B.

TABLE B

| Exp. No. | Temp. °C. | Time, hr. | Conversion, % | Selectivity methacrylic acid | acetic acid | CO + $CO_2$ |
|---|---|---|---|---|---|---|
| 1 | 306 | 14 | 71.5 | 85.8 | 3.6 | 0.41 |
| 2 | 306 | 16 | 72 | 82.2 | 5.5 | 0.68 |
| 3 | 302 | 36 | 76 | 85.4 | 2.94 | 0.67 |
| 4 | 302 | 38 | 78 | 85.3 | 3.55 | 0.69 |
| 5 | 304 | 52 | 80 | 86.17 | 3.72 | 0.57 |
| 6 | 303 | 56 | 75 | 87.0 | 3.1 | 0.52 |
| 7 | 304 | 60 | 75 | 86.4 | 2.53 | 0.57 |
| 8 | 305 | 86 | 62 | 85.5 | 4.1 | 0.42 |
| 9 | 304 | 88 | 74 | 86.6 | 3.8 | 0.46 |
| 10 | 304 | 90 | 64 | 85.1 | 3.9 | 0.43 |
| 11 | 304 | 92 | 67 | 84.97 | 5.6 | 0.41 |
| 12 | 304 | 96 | 72 | 84.67 | 4.0 | 0.45 |
| 13 | 304 | 98 | 62 | 85.90 | 3.8 | 0.46 |
| 14 | 305 | 100 | 58 | 86.07 | 3.6 | 0.45 |
| 15 | 303 | 102 | 60 | 86.27 | 3.3 | 0.45 |
| 16 | 304 | 104 | 61 | 86.7 | 3.1 | 0.46 |
| 17 | 303 | 107 | 63 | 85.8 | 4.4 | 0.49 |
| 18 | 302 | 111 | 56 | 86.04 | 3.5 | 0.45 |

EXAMPLE III

A catalyst is prepared as described in Example I except that the boron component is omitted and, in the resulting catalyst, the components molybdenum, copper, vanadium, antimony, cesium and phosphorus are present in the atomic ratios of 12, 0.3, 0.3, 0.3, 1 and 1, respectively. The oxidation is carried out as described in Example I except that the temperature ranged from 275° C. to 285° C., the lower temperatures being used in order to obtain conversion values comparable to those shown in Examples I and II. The results of these experiments are set forth in Table C.

TABLE C

| Exp. No. | Temp. °C. | Time, hr. | Conversion, % | Selectivity methacrylic acid | acetic acid | CO + $CO_2$ |
|---|---|---|---|---|---|---|
| 1 | 284 | 8 | 64 | 79.7 | 5.03 | 0.70 |
| 2 | 285 | 10 | 65 | 82.02 | 5.24 | 0.68 |
| 3 | 284 | 12 | 67 | 77.08 | 4.8 | 0.87 |
| 4 | 284 | 14 | 65 | 78.1 | 4.5 | 0.9 |
| 5 | 280 | 16 | 58 | 80.5 | 4.82 | 0.7 |
| 6 | 280 | 18 | 52.8 | 80.7 | 4.5 | 0.75 |
| 7 | 275 | 28 | 56.1 | 80.7 | 4.6 | 0.61 |
| 8 | 278 | 30 | 58 | 79.4 | 4.7 | 0.61 |
| 9 | 279 | 32 | 60 | 77.4 | 4.9 | 0.75 |
| 10 | 275 | 36 | 56 | 79.4 | 5.66 | 0.66 |
| 11 | 279 | 50 | 53 | 80.7 | 3.9 | 0.54 |
| 12 | 278 | 54 | 57 | 79.3 | 4.3 | 0.53 |

The embodiments of the invention in which an exclusive property is claimed are defined as follows:

1. A catalyst composition suitable for the vapor-phase oxidation of an unsaturated aldehyde to produce the corresponding unsaturated acid consisting essentially of oxides of molybdenum, copper, boron, phosphorus and antimony, an alkali metal and optionally vanadium wherein the molybdenum, copper, boron, phosphorus, antimony, alkali metal and vanadium are present in the atomic ratios of 12, 0.05-3, 0.001-3, 0.1-5, 0.01-1, 0.05-5 and 0-5 respectively.

2. A catalyst composition as defined in claim 1, wherein the amount of antimony is 0.2-0.4.

3. A catalyst composition as defined in claim 2, wherein the amount of alkali metal is at least 0.05.

* * * * *